United States Patent [19]

Firicá et al.

[11] Patent Number: 4,915,092
[45] Date of Patent: Apr. 10, 1990

[54] FLEXIBLE IMPLANTS FOR STABLE FLEXIBLE OSTEOSYNTHESIS OF FEMORAL TIBIA FRACTURES AND WORKING INSTRUMENTATION

[75] Inventors: Andrei Firicá; Alexandru I. B. Manov; Dragos Gheorghiu, all of Bucharest, Romania

[73] Assignee: Interprinderea Industria Technico-Medicala, Bucharest, Romania

[21] Appl. No.: 366,304

[22] Filed: Jun. 13, 1989

Related U.S. Application Data

[63] Continuation of Ser. No. 97,968, filed as PCT RO86/0000 on Sept. 18, 1986, published as WO87/02572 on May 7, 1987, abandoned.

[30] Foreign Application Priority Data

Nov. 5, 1985 [RO] Romania .................. 120633

[51] Int. Cl.$^4$ ................................. A61F 5/04
[52] U.S. Cl. ........................... 606/67; 606/64
[58] Field of Search ........ 128/92 YK, 92 YZ, 92 VT, 128/92 YV, 92 YW, 92 YS, 92 YF, 92 VK

[56] References Cited

U.S. PATENT DOCUMENTS

| 4,055,172 | 10/1977 | Ender et al. | 128/92 VT |
| 4,135,507 | 1/1979 | Harris | 128/92 YZ |
| 4,169,470 | 10/1979 | Ender et al. | 128/92 YZ |
| 4,381,770 | 5/1983 | Neufeld | 128/92 YK |
| 4,467,793 | 8/1984 | Ender | 128/92 YZ |
| 4,473,069 | 9/1984 | Kolmert | 128/92 YZ |
| 4,483,335 | 11/1984 | Tornier | 128/92 YK |
| 4,503,847 | 3/1985 | Mouradian | 128/92 YZ |
| 4,570,623 | 2/1986 | Ellison et al. | 128/92 YC |
| 4,667,663 | 5/1987 | Miyata | 128/92 YZ |

FOREIGN PATENT DOCUMENTS

| 2483214 | 12/1981 | France | 128/92 YV |
| 74202 | 5/1980 | Romania . | |
| 576249 | 6/1976 | Switzerland | 128/92 YZ |

OTHER PUBLICATIONS

Pp. 75, 76, Rob. Mathys Co. Instrumentenfabric Catalog 1977.
5 pages from leaflet Küntscher Catalog.

*Primary Examiner*—Robert A. Hafer
*Assistant Examiner*—Charles H. Sam
*Attorney, Agent, or Firm*—Herbert Dubno

[57] ABSTRACT

A set of flexible implants for repair of femur fractures includes a short implant which is of flattened S shape and is dimensioned to extend generally upwardly from a point below the upper condyle through the neck and into the head of the femur, an intermediate length pin which is bowed to be turned downwardly and to extend from a region below the short pin through the neck and into the head of the femur, and a long pin which is bowed and extends the length of the femur from the region of the lower condyle into the upper condyle or the head of the femur. Short and intermediate length pins have eyes adapted to lie against the shank of the femur and are held in place by bone nails or screws. The lower end of the long pin has an S bend connected to a spade formation conforming to the curvature of the region of the long pin.

1 Claim, 2 Drawing Sheets

FLEXIBLE IMPLANTS FOR STABLE FLEXIBLE OSTEOSYNTHESIS OF FEMORAL TIBIA FRACTURES AND WORKING INSTRUMENTATION

This is a continuation of co-pending application Ser. No. 097,968, filed as PCT RO86/00001 on Sept. 18, 1986, published as WO87/02572 on May 7, 1987, and now abandoned.

FIELD OF THE INVENTION

Our present invention relates to a set of flexible implants for promoting osteosynthesis and repair of fractures, particularly femural fractures.

BACKGROUND OF THE INVENTION

Fractures of the femur frequently are problematical because they may involve fractures of the neck separating the head from the femur, fractures separating the head and upper condyle region from the femur and fractures along the shank of the femur.

Various implants have been designed for pinning the fractured portions together, although these were not always fully satisfactory.

OBJECT OF THE INVENTION

It is, therefore, the object of this invention to provide an improved set of implants for overcoming the aforementioned drawback.

SUMMARY OF THE INVENTION

This object and others which will become apparent hereinafter are attained, in accordance with this invention by providing a three-pin set of implants including a short pin which overall has a generally S-shaped curvature with a point region extending away from a shank opposite the direction in which an eye extends therefrom, an intermediate length implant in which the point is formed at the end of a bowed region and at an opposite end of which an S-bend is provided to terminate in an eye, and a long implant which, like the intermediate implant, is generally bowed with an S-shaped bend at its end opposite the point, but has a spade-shaped formation rounded to lie in surface contact with the bone at the junction of the lower condyles with the shank of the femur.

A short implant is dimensioned to extend through the neck into the head immediately below the upper condyle while the intermediate-length implant is dimensioned to pass through the neck and into the head from the side of the shank opposite the neck below the short implant, the eyes receiving respective bone screws or nails for attachment to the femur. The long implant is dimensioned to extend through the bone over substantially the full length of the shank and either into the head or the upper condyle.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 1:
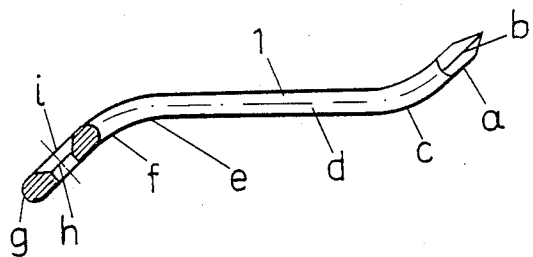
FIG. 1 is an elevational view of the short bone of the set of implants according to the invention, showing the eye in section.
Figure 7:
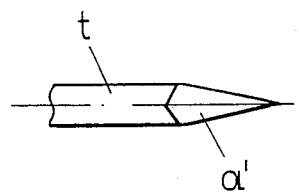
FIG. 7 is an elevational view of the point of the longer implant, drawn to a larger scale than FIG. 4.
Figure 8:
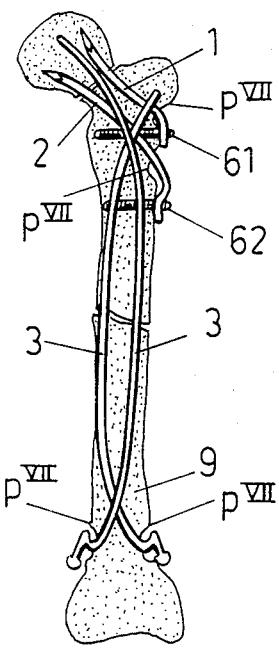
FIG. 8 is a diagram showing the use of the set of the invention in the repair of a multiple fracture according to one embodiment of the invention.
Figure 9:
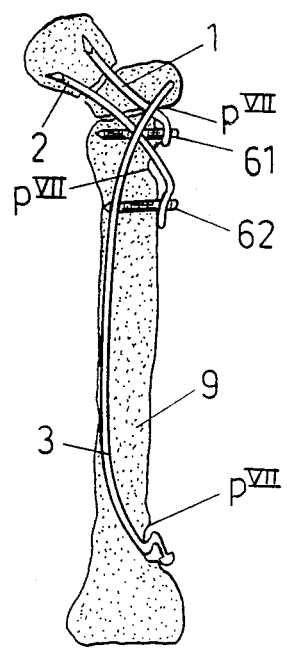
FIG. 9 is a view similar to FIG. 8 illustrating another fracture repair.

FIGS. 1, 8 and 9 show the short pin 1 of the set of flexible implants of the invention, this pin having a shank d which can be straight (FIG. 1) or slightly bent (FIGS. 8 and 9) terminating in oppositely directed bends c and e, so that the overall shape of this short pin is that of a flattened S. The bend c terminates in a point a which has a triangular cross section (see the point a' of FIG. 7) at its opposite end, the bend e merges with a flat or planar structure f including an eye g which has a hole h provided with a countersink i for receiving the nail or screw 61 which can be driven into the shank of the bone of the femur 9 below the upper condyle and into the head of the femur, passing through the neck in the case of a neck fracture and also serving in the case of a fracture across the shank below the upper condyle (FIG. 9). The pin is turned upwardly when inserted into the bone in this manner.

The intermediate length pin 2 has a bowed shank m forming a transition l with a point j which can have the triangular section represented by the ridge k as previously desribed.

Figure 3:
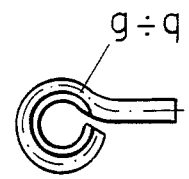
FIG. 3 is an elevational view of the eye of FIG. 1 or FIG. 2.
Figure 2:
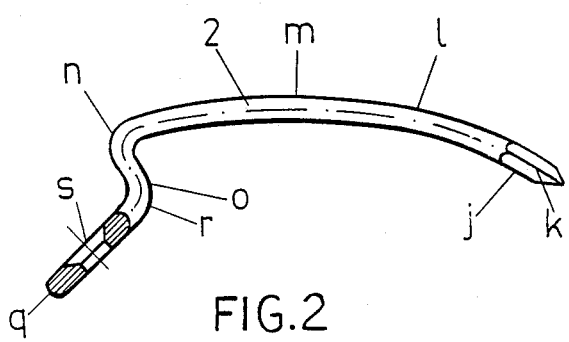
FIG. 2 is a view similar to FIG. 1 of the intermediate length implant.

At its opposite end, the bowed shank 2 forms an S-bend with the eye g including bends n and o before forming the planar portion r. The holes in the eye are represented at s and the eye is seen in elevation in FIG. 3.

From FIGS. 8 and 9, it will be apparent that the pin 2 is turned downwardly in the insertion into the femur, although it extends also into the head of the femur through the neck from the opposite side of the shank, below the upper pin 1. Recesses $p^{VII}$ are provided in the bone to permit guidance of the pins into place. A bone nail or screw 62 traverses the eye g as previously described.

The long implant 3 has a shank t of a length such that the implant can extend the full height of the shank of the femur (see FIGS. 8 and 9) and terminates at its upper end in a bend as a point u having a triangular tip a' (FIG. 7).

Figure 5:
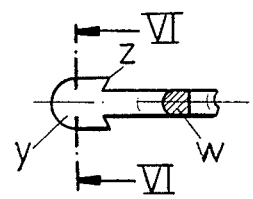
FIG. 5 is an elevational view of the spade region thereof.
Figure 4:
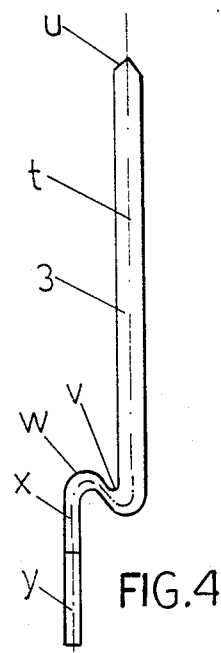
FIG. 4 is a side elevational view of the long implant, somewhat contracted in length.
Figure 6:
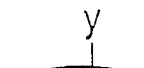
FIG. 6 is a sectional view taken along the line VI—VI of FIG. 5 and drawn to a larger scale.

At its opposite end, through an S bend w, with portions v and x, respectively, the implant 3 extends into a spade formation y which is upwardly convex and inwardly concave so as to fit closely against the shank of the bone immediately adjoining one of the lower condyles. The spade formation has barbs z as can be seen best in FIG. 5. In FIGS. 8 and 9, the spade formations are rotated out of their normal lie for illustration purposes.

From FIGS. 8 and 9 it will be apparent that one or two such pins 3 can extend upwardly from the junctions with the lower condyles through the shank of the femur into either the upper condyle (FIG. 9) or the head via the neck (FIG. 8).

We claim

1. A set of flexible bone implants for repair of a femural fracture, said set comprising:
   a short pin of generally serpentine shape having an elongated, straight central portion with oppositely directed shorter-length bends at opposite ends thereof, one of said bends terminating in a generally triangular point, the other of said bends terminating in a bent-wire, closed circular eye lying in a plane and through which a bone nail can be inserted to hold said eye flush against a shank of a femur bone below an upper condyle thereof when said short pin is inserted through a neck of said femur into a head thereof;
   an intermediate-length pin having a bowed central portion formed at one end with a generally triangular point, and at an opposite end with a second bent-wire, closed circular eye connected thereto through an S-curved bend, said intermediate length pin being of a length sufficient to enable insertion through said femur and said neck into said head and disposed below said short pin, and can be anchored flush to said femur by another bone nail or screw inserted through the second eye of said intermediate-length pin; and
   a long pin of a length sufficient to enable it to pass through the full length of said shank of said femur from a region adjacent a lower condyle thereof into said upper condyle or said femoral head, said long pin having a body formed by an elongated, straight portion terminating respectively at a forward end in a generally triangular point and at an opposite rear end, through a second S-curved bend, in a widened spade-shaped, non-perforated formation having a forwardly directed barb disposed on either side of a longitudinal axis of said formation, said formation being arcuately bent about said longitudinal axis thereof to conform to the curvature of the femur at said region and adapted to rest thereon, said second S-curve formed by a pair of oppositely directed curves each having a respective inner curve lying tangent to a line running substantially transverse to a longitudinal direction of said body.

* * * * *